（12）United States Patent
Nakamura

(10) Patent No.: US 8,662,074 B2
(45) Date of Patent: *Mar. 4, 2014

(54) GAS MIST INHALER

(75) Inventor: Shoichi Nakamura, Higashichikuma-gun (JP)

(73) Assignees: ACP Japan Co., Ltd., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 188 days.

This patent is subject to a terminal disclaimer.

(21) Appl. No.: 12/998,648

(22) PCT Filed: May 18, 2010

(86) PCT No.: PCT/JP2010/058375
§ 371 (c)(1),
(2), (4) Date: May 13, 2011

(87) PCT Pub. No.: WO2010/137493
PCT Pub. Date: Dec. 2, 2010

(65) Prior Publication Data
US 2011/0220101 A1    Sep. 15, 2011

(30) Foreign Application Priority Data
May 29, 2009   (JP) ................. 2009-130997

(51) Int. Cl.
*A61M 11/00*   (2006.01)
(52) U.S. Cl.
USPC ............ 128/200.21; 128/200.14; 128/200.18; 128/203.12
(58) Field of Classification Search
USPC ............. 128/200.11–200.13, 200.14–200.23, 128/203.12–203.14, 203.16–203.17, 204.14
See application file for complete search history.

(56) References Cited

U.S. PATENT DOCUMENTS

| | | | | |
|---|---|---|---|---|
| 4,051,847 | A | * | 10/1977 | Henkin .................... 128/202.22 |
| 5,156,776 | A | * | 10/1992 | Loedding et al. ............... 261/27 |
| 5,915,377 | A | * | 6/1999 | Coffee ..................... 128/200.16 |

(Continued)

FOREIGN PATENT DOCUMENTS

| | | |
|---|---|---|
| JP | H10-211284 | 8/1998 |
| JP | 2004-242737 | 9/2004 |
| JP | 2007-014482 | 1/2007 |
| JP | 2008-220661 | 9/2008 |

*Primary Examiner* — Kevin C Sirmons
*Assistant Examiner* — Valerie L Skorupa
(74) *Attorney, Agent, or Firm* — Manabu Kanesaka

(57) ABSTRACT

The present invention is to provide a gas mist inhaler making use of physiological actions of carbon dioxide or oxygen, which is simple in a structure and excellent in effects. The gas mist inhaler is composed of a gas mist inhaler which comprises; a gas supply means 11 for supplying oxygen, carbon dioxide, otherwise a mixed gas (called as "gas" hereafter) of oxygen and carbon dioxide; a first and a second liquid supply means 21A, 12B for supplying a first and a second liquids; a gas mist generation means 31 for generating a mist (called as "gas mist" hereafter) which is prepared by pulverizing and dissolving the gas, the first and the second liquids; an inhalation mask 71 having an inhalation port 72 for inhaling the generated gas mist into a living organism; a liquid circulation means 41 where the liquid collected in the gas mist generation device 31 is again supplied under pressure into the gas mist generation device 31; and the above mentioned gas mist is inhaled into any one or both of an upper air way or a lower air way of the living organism.

10 Claims, 7 Drawing Sheets

(56) References Cited

U.S. PATENT DOCUMENTS

| | | | |
|---|---|---|---|
| 7,415,980 B2* | 8/2008 | Hashiba | 128/200.21 |
| 2003/0196664 A1* | 10/2003 | Jacobson | 128/206.21 |
| 2004/0050383 A1* | 3/2004 | Cox et al. | 128/200.14 |
| 2009/0235925 A1* | 9/2009 | Power et al. | 128/200.14 |
| 2011/0108025 A1* | 5/2011 | Fink et al. | 128/200.16 |

* cited by examiner (a)

(b)

(a)

(b)

GAS MIST INHALER

RELATED APPLICATIONS

The present application is National Phase of International Application No. PCT/JP2010/058375 filed May 18, 2010, and claims priority from, Japanese Application No. 2009-130997 filed May 29, 2009, the disclosure of which are hereby incorporated by reference herein in its entirety.

TECHNICAL FIELD

The present invention relates to a gas mist inhaler for carrying out oral inhalation of a gas mist into a living organism, which is prepared by pulverizing and dissolving oxygen, carbon dioxide, or a mixed gas of oxygen and carbon dioxide, and a liquid such as a medicine.

BACKGROUND ART

It has conventionally been known that if carbon dioxide (carbonic acid anhydride: $CO_2$) contacts the skin and the mucous membrane of the living organism, it penetrates into them only thereby, and it expands blood vessels around the parts of penetrated carbon dioxide and works to improve the blood circulation. Owing to this action of accelerating the blood circulation, carbon dioxide displays various physiological effects such as dropping of blood pressure, improving of metabolism or accelerating to remove pain substance or waste products. Further, it has also anti-inflammation and anti-bacterial. Therefore, carbon dioxide has recently been given attentions also from viewpoints of improving health or beauty other than the purpose of medical cares.

Carbon dioxide in the tissue of the living organism works to release oxygen having been carried in combination with hemoglobin in a red blood cell. Around parts at a high density of carbon dioxide, the red blood cell releases more oxygen. Thus, supply of oxygen to cells by the red blood cell is mainly controlled by carbon dioxide. In short, being without carbon dioxide, hemoglobin remains as having been combined with oxygen and the cell becomes unable to receive oxygen. As is seen, carbon dioxide seems to be a waste product resulted from action of the cell, however, it plays in fact very important roles in the living organism.

Further, in recent times, oxygen of the high density has also widely been known as effective in activity of metabolism, fatigue recovery, or stability of blood pressure. Other than them, oxygen has also effects of disinfection or sterilization by oxidation.

By the way, for easing a symptom of disease in a respiratory system such as asthma or allergic rhinitis, an oral inhalation or nasogastric inhalation using an inhaler or rhinenchysis spray have been till now operated.

Recently, a nasogastric vaccine (spray type nose vaccine) for forming a mucous membrane immunity to influenza virus has been developed and its high effect has been given attention. This nasogastric vaccine is higher in the effect preventing an influenza crisis than a vaccine of a hypodermic injection, and being different from an injection type, it has merits working effectively to various virus roots. Also in prevention or curing against influenza, antiviral drugs by an inhalation dosage have been developed.

SUMMARY OF INVENTION

Problems to be Solved by the Invention

However, there has never been appeared an inhaler which dissolves carbon dioxide or oxygen in the medicine as above mentioned and can influence physiological actions of a gas to the living organism.

In view of the above circumstances, the present invention is to provide a gas mist inhaler making use of physiological actions of carbon dioxide or oxygen, which is simple in a structure and excellent in effects.

Means for Solving the Problems

For solving the above mentioned problems, the present invention is to provide a gas mist inhaler which comprises a gas supply means for supplying oxygen, carbon dioxide, otherwise a mixed gas (called as "gas" hereafter) of oxygen and carbon dioxide, a first and a second liquid supply means for supplying a first and a second liquids, a gas mist generation means for generating a mist (called as generation "gas mist" hereafter) which is prepared by pulverizing and dissolving the above gas, the above first and second liquids, an inhalation member having an inhalation port for inhaling the gas mist into a living organism, and a liquid circulation means where the liquid collected in the gas mist generation means is again supplied into the gas mist generation means, characterized by inhaling the above gas mist into any one or both of an upper air way or a lower air way of the living organism.

By the way, the invention refers it as "pulverizing and dissolving" to pulverize the liquid into fine liquid drops, and cause to contact and mix with gas (carbon dioxide, oxygen, or the mixed gas of carbon dioxide and oxygen).

Herein, it is sufficient to further provide a sensor of measuring conditions of supplying the gas, liquid and gas mist as well as a control means basing on the measuring values of the sensor to carry out supply controls of the gas and the liquid and to carry out generation and supply control of the gas mist.

It is suitable to further provide a liquid pressure means of supplying under pressure the liquid circulated by the liquid circulation means into the gas mist generation means.

It is also good to provide a charging device of giving charge to the mist supplied by the gas mist generation means. At this time, the charge is preferably minus.

The above mentioned first and second liquids are desirable to be any one or plural combination of water, ionic water, ozone water, physiological salt solution, purified water or sterilized and purified water, and those are preferable to contain any one or plural combination of menthol, vitamin E, vitamin C derivative, retinol, anesthetic, cyclodextrin, photocatalyst, complex of photocatalyst and apatite, hyaluronic acid, coenzyme Q10, seed oil, propolith, silica, povidone-iodine, anti-allergic agent, anti-inflammatory agent, anti-febrile, anti-fungus agent, anti-influenza virus, influenza vaccine, steroid agent, anti-cancer substance, or anti-hypertensive agent.

The gas mist generation means has a gas mist supply pipe of connecting the inhalation member to the gas mist generation means in order to supply the gas mist, and this gas mist supply pipe has preferably a filter to remove liquid drops attached to the inside of the pipe. Further, a whole or one part of the gas mist supply pipe is suitably composed of a cornice shaped pipe, and this gas mist supply pipe is provided with a check valve. At this time, it is also good to connect the gas mist generation means to plural inhalation members by the gas mist supply pipe.

Further, the gas mist generation means has a tank of storing the liquid and the gas mist, and this tank is desirably placed inside with one or plurality of pored plates for refining the gas mist.

Advantageous Effect of the Invention

According to the gas mist inhaler of the invention, adding to ordinary effects of the inhaler, by the physiological action of the gas mist, not only permeating a liquid medicine into the upper and lower airways of the living organism, but also activating a blood flow around a diseased part, the invention can display effects such as flourishing the blood flow of the disease, rapidly moderating an inflammation or increasing immunological force.

DESCRIPTION OF EMBODIMENTS

In the following description, explanations will be made to the embodiments of this invention, referring to the attached drawings.

Figure 1:
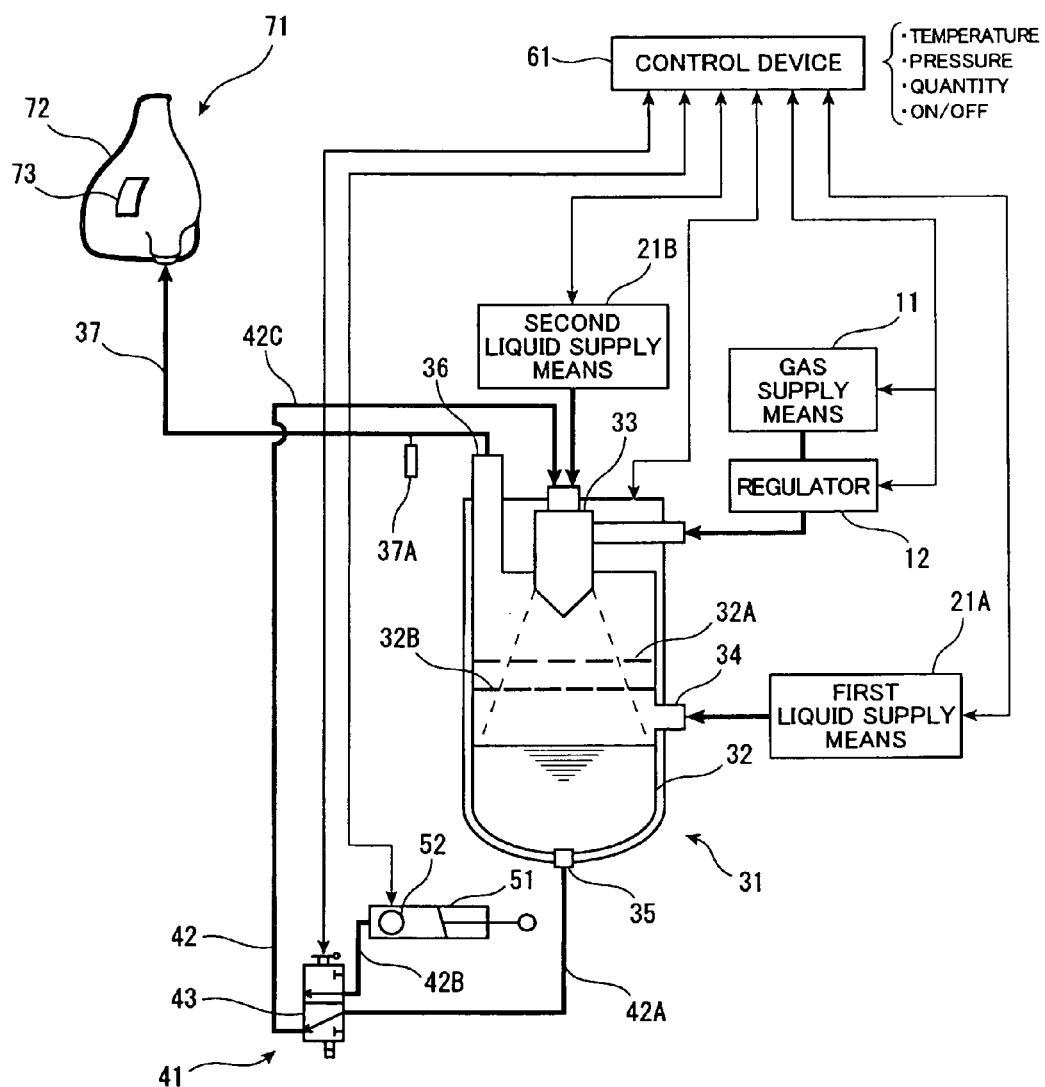
FIG. 1 A schematic view showing the whole structure of the gas mist inhaler depending on one embodiment of the invention.

FIG. 1 is the schematic view showing the whole structure of the gas mist inhaler depending on one embodiment of the invention. As shown in FIG. 1, the gas mist inhaler 1 of the present embodiment is composed of a gas mist inhaler which comprises a gas supply means 11 for supplying oxygen, carbon dioxide, otherwise a mixed gas (called as "gas" hereafter) of oxygen and carbon dioxide; a first and a second liquid supply means 21A, 21B; a gas mist generation device 31 for generating a mist (called as "gas mist" hereafter) which is prepared by pulverizing and dissolving the gas, the first and the second liquids; a liquid circulation means 41; a liquid pressurizer 51 where the liquid collected in the gas mist generation device 31 is again supplied under pressure into the gas mist generation device 31; a control device 61 of carrying out generation control and supply control of the gas mist; and an inhalation mask (inhalation member) 71 for inhaling the generated gas mist into the living organism.

The gas supply means 11 supplies oxygen, carbon dioxide, otherwise oxygen and carbon dioxide to the gas mist generation means. If supplying oxygen as a gas, a suitable density of oxygen is around 40 to 98%. As the gas supply means 11, a gas bomb is used, and the gas supply means 11 is furnished with a regulator 12 for adjusting pressure of gas. Omitting an illustration, the gas supply means 11 may have a heater for heating gas and a thermometer for controlling temperatures.

The first and second liquid supply means 21A, 21B are composed of pumps and respectively supply the liquid to the gas mist generation device 31. It is preferable to employ water, ionic water, ozone water, physiological salt solution, purified water or sterilized and purified water. In addition, these liquids may contain medicines effective to users' diseases or symptoms. For the medicines, there are enumerated, for example, anti-allergic agent, anti-inflammatory agent, anti-febrile and analgesic, anti-fungus agent, anti-influenza viral agent, influenza vaccines, steroid substance, anti-cancer drug, anti-hyper tensile agent. Further, these liquids are mixed with single or plurality of menthol having a cooling action; vitamin E accelerating circulation of the blood; vitamin C derivative easily absorbed to a skin tissue and having a high skin beautifying effect; retinol normalizing a skin heratinizing action and protecting the mucous membrane; anaesthetic moderating irritation to the mucous membrane; cyclodextrin removing odor; photocatalysis having sterilizing and anti-phlogistic effect or a complex of photocatalysis and apatite; hyaluronic acid having excellent water holding capacity and a skin moisture retention effect; coenzyme Q10 activating cells and heightening immunization; a seed oil containing anti-oxidation substance, or much nutrient; propolith having anti-oxidation function, anti-fungus function, anti-inflammatory function, pain-killing function, anesthetic function, and immunity function. Thus, those substances are possible to generate synergistic effects by coupling with a gas physiological action. Otherwise, it is possible to add silica or povidone-iodine.

The liquid of the second liquid supply means 21B is supplied to the fluid nozzle 33 of the gas mist generation device 31. The liquid of the first liquid supply means 21A is supplied from the fluid supply port 34 of the gas mist generation device 31. By the way, it is desirable that the first and second liquid supply means 21A, 21B are respectively arranged with heaters (not shown) for heating the liquid and supplying (for example, heating water up to hot water at around 40° C.) or thermometers (not shown) controlling temperatures.

The gas mist generation device 31 has a tank 32 of storing the liquid and the gas mist, a fluid nozzle 33 of generating the gas mist from the liquid and the gas, this liquid being supplied from the second liquid supply means 21B and the liquid pressurizer 51 and this gas being supplied from the gas supply means 11, a liquid supply port 34 of storing the liquid from the first liquid supply means 21A into the tank 32, a liquid discharge port 35 of sending the liquid collected in the tank 32 into a liquid circulation circuit 42, a gas mist discharge port 36 of discharging the gas mist in the tank 32, and a gas mist supply pipe 37 of supplying the gas mist from the gas mist discharge port 36 into the inhalation mask 71.

Figure 2:
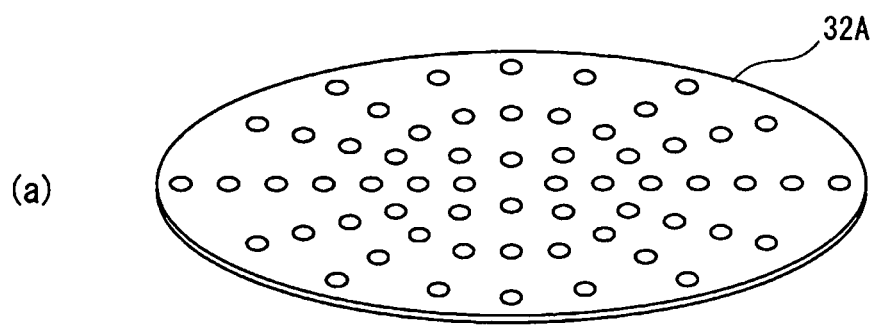
FIG. 2 A typical view showing one example of plates to be placed within the gas mist generation device of the gas mist inhaler of the invention.
Figure 2:
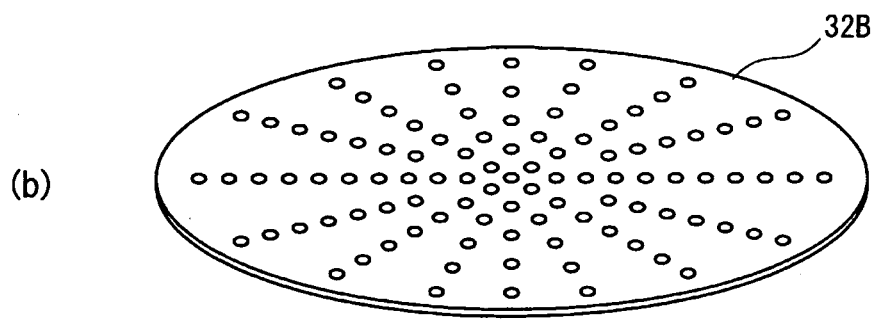

Inside of the tank 32, for refining the generated gas mist, there may be furnished one or plural sheets (in FIG. 1, two sheets as an example) of plates 32A, 32B above the surface of the stored liquid. FIG. 2 shows the plates 32A, 32B. Thus, the plates 32A, 32B are formed with plural narrow pores, and when passing through these narrow pores, the generated gas mist is refined. With respect to the plate 32A being near to the fluid nozzle 33 and the plate 32B being far therefrom, the diameters of the pores of the far plate 32B are made smaller than those of the pores of the near plate 32A.

The fluid nozzle 33 (herein, as an example, 3-fluid nozzle) makes use of gas high speed flow from the gas supply means 11 to pulverize and dissolve the liquid into the gas mist. This time, the liquid drop finely pulverized can display an effect of minus ion.

The tank 32 is filled with the gas mist generated by the fluid nozzle 33 together with the liquid supplied via the liquid supply port 34 from the first liquid supply means 21A. The filled gas mist is supplied into the inhalation mask 71 via the gas mist supply pile 37 from the gas mist discharge port 36, and one part of the gas mist fuses into the liquid stored in the tank 32. Therefore, the liquid collected in the tank 32 becomes gradually higher in a gas dissolving density. This liquid is further circulated by a liquid circulation means 41. That is, the liquid collected in the tank 32 is led into the fluid nozzle 33 through the liquid circulation circuit 42 and turned out into the gas mist, and by repeating the circulation, it is possible to generate the gas mist dissolved with the gas at high density.

The liquid circulation means 41 is composed of the liquid circulation circuit 42 and a valve 43. The liquid circulation circuit 42 is a circuit for conveying the liquid which is connected to the liquid pressurizer 51 from the liquid discharge port 35 of the gas mist generation device 31 as well as to the fluid nozzle 33. The liquid circulation circuit 42 is provided with the valve 43 to enable to switch to any of a circuit connecting the liquid discharge port 35 and the fluid nozzle 33, a circuit connecting the liquid discharge port 35 and the liquid pressurizer 51, and a circuit connecting the liquid pressurizer 51 and the fluid nozzle 33. It is also enough to concurrently switch both of the liquid discharge port 35 and the fluid nozzle 33, and the liquid discharge port 35 and the liquid pressurizer 51. For circulating the liquid within the tank 32 into the fluid nozzle 33, the liquid passes in succession in the order from the liquid discharge port 35 to a first liquid conduit line 42A, the valve 43 and a third liquid conduit line 42C, and gets to the fluid nozzle 33. For filling the liquid within the tank 32 into the liquid pressurizer 51, the liquid passes in succession in the order from the liquid discharge port 35 to the first liquid conduit line 42A, the valve 43 and a second liquid conduit line 42B, and gets to the liquid pressurizer 51. For sending the liquid filled in the liquid pressurizer 51 to the fluid nozzle 33, the liquid passes in succession in the order from the liquid pressurizer 51 to the second liquid discharge port 42B, the valve 43 and the third liquid conduit line 42C, and gets to the fluid nozzle 33.

The gas mist discharged from the gas mist discharge port 36 of the gas mist generation device 31 is supplied from the gas mist supply pipe 37 into the inhalation mask 71. The gas mist supply pipe 37 has a liquid drop removing filter 37A for removing droplets attached to the inside of the pipe. Although not illustrating, the gas mist supply pipe 37 is provided inside with a check valve for checking back-flow of the gas mist and the gas.

Figure 3:
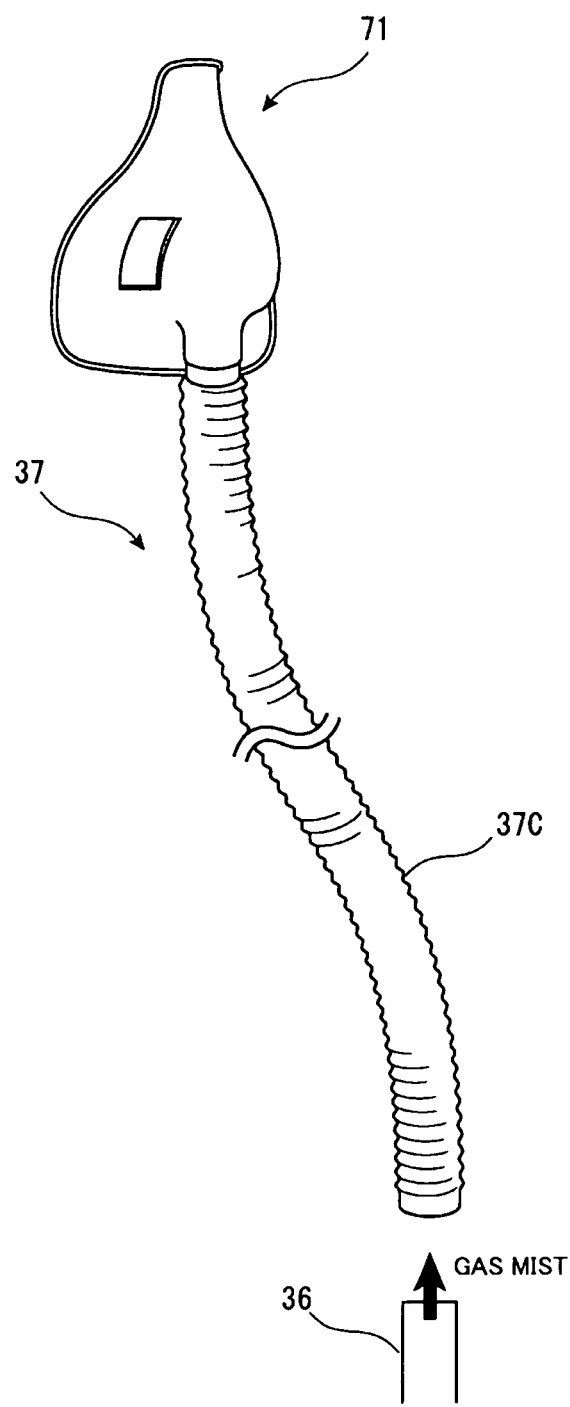
FIG. 3 A typical view showing one example of the gas mist inhalation pipe used to the gas mist inhaler of the invention.

Further, as shown in FIG. 3, preferably, the gas mist supply pipe 37 is overall or partially composed of a soft cornice shaped pipe 37C of a large diameter. If composing of such a cornice shaped pipe 37C, the gas mist supply pipe 37 is freely bent and may be expanded so that a user of this system is not restricted in his action. Even if the gas mist flowing in the gas mist supply pipe 37 becomes gradually liquefied, the liquid can be removed through the concave and convex of the cornice.

The liquid pressurizer 51 is composed of, e.g., a pump, and after the liquid is collected in the tank 32 of the gas mist generation device 31, fully dissolved with the gas and filled, the liquid pressurizer supplies under pressure this filled liquid to the fluid nozzle 33 of the gas mist generation device 31. Thereby, inside of the tank 32 of the gas mist generation device 31, the gas mist more dissolved with the gas is generated, and it is possible to push out the gas mist stored in the tank 32 toward the gas mist discharge port 36. The liquid pressurizer 51 is provided with a manometer 52 for adjusting pressure.

The control device 61 is desirably composed of a computer furnished with CPU, memory and display. This control device 61 performs various kinds of controls for carrying out pressure or on-off switch of the gas from the gas supply means 11; amount, pressure, temperature or on-off switch of supply of the liquid from the liquid supply means 21; on-off switch of supply of the gas mist from the gas mist generation device 31; switch of the valve 43; and pressure or on-off switch of the liquid pressurizer 51. Thus, the inhalation of the gas mist can be performed under an optimum condition.

The gas mist inhaler 1 of the present invention is desirably provided with a part of setting gas supply pressure other than the power supply switch, though not illustrating. It is thereby possible to reply a user's purpose or use such as an optimum inhalation even if using plural inhalation members as later mentioned. Further, it is also possible to set a gas supplying time by providing an off-timer. In short, when passing after the time set by the off timer, the gas supply can be automatically stopped.

The inhalation mask 71 is an inhalation member having a shape covering a user's inhaler (herein, the nose and mouth) for the user to easily breathe the gas mist generated in the gas mist generation device 31. The inhalation mask 71 is connected to the gas mist discharge port 36 of the gas mist generation device 31 via the gas mist supply pipe 37, and the user breathes the gas mist from the inhalation port 72. The inhalation mask 71 is preferably formed with an opening port 73 for taking in outside air and avoiding evils by breathing oxygen of high density or carbon dioxide for a long time.

For carrying out the inhalation of the above mentioned gas mist using the gas mist inhaler 1 of this embodiment, the liquid is supplied from the first liquid supply means 21A into the gas mist generation device 31 and is stored in the tank 32. Subsequently, the liquid is supplied into the fluid nozzle via the first liquid conduit line 42A, the valve 43 and the third liquid conduit line 42C from the liquid discharge port 35, pulverized and dissolved with the gas from the gas supply means 11 in order to generate the gas mist. Thus, by holding, for a certain time, a circulating condition that the liquid is caused by the liquid circulation means 41 to pass from the tank 32 through the liquid circulation circuit 42 and the fluid nozzle 33 and again goes back to the tank 32, the gas dissolving density of the liquid is heightened. Next, the liquid is supplied to the liquid pressurizer 51 via the first liquid conduit line 42A, the valve 43 and the second liquid conduit line 42B from the liquid discharge port 35. When the liquid is fully filled in the liquid pressurizer 51, the supply is stopped. The liquid is supplied under pressure into the fluid nozzle 33 via the second liquid conduit line 42B, the valve 43 and the third liquid conduit line 42C from the liquid pressurizer 51 in order to generate the gas mist, and at the same time the gas mist collected in the tank 32 is discharged from the gas mist discharge port 36. The discharged gas mist goes from the gas mist supply pipe 37 to the inhalation mask 71, and is inhaled to the user from the inhalation port 72.

The above reference has shown the example of using the inhalation mask 71 covering the nose and the mouth, and other various types using the inhalation members are available.

Figure 4:
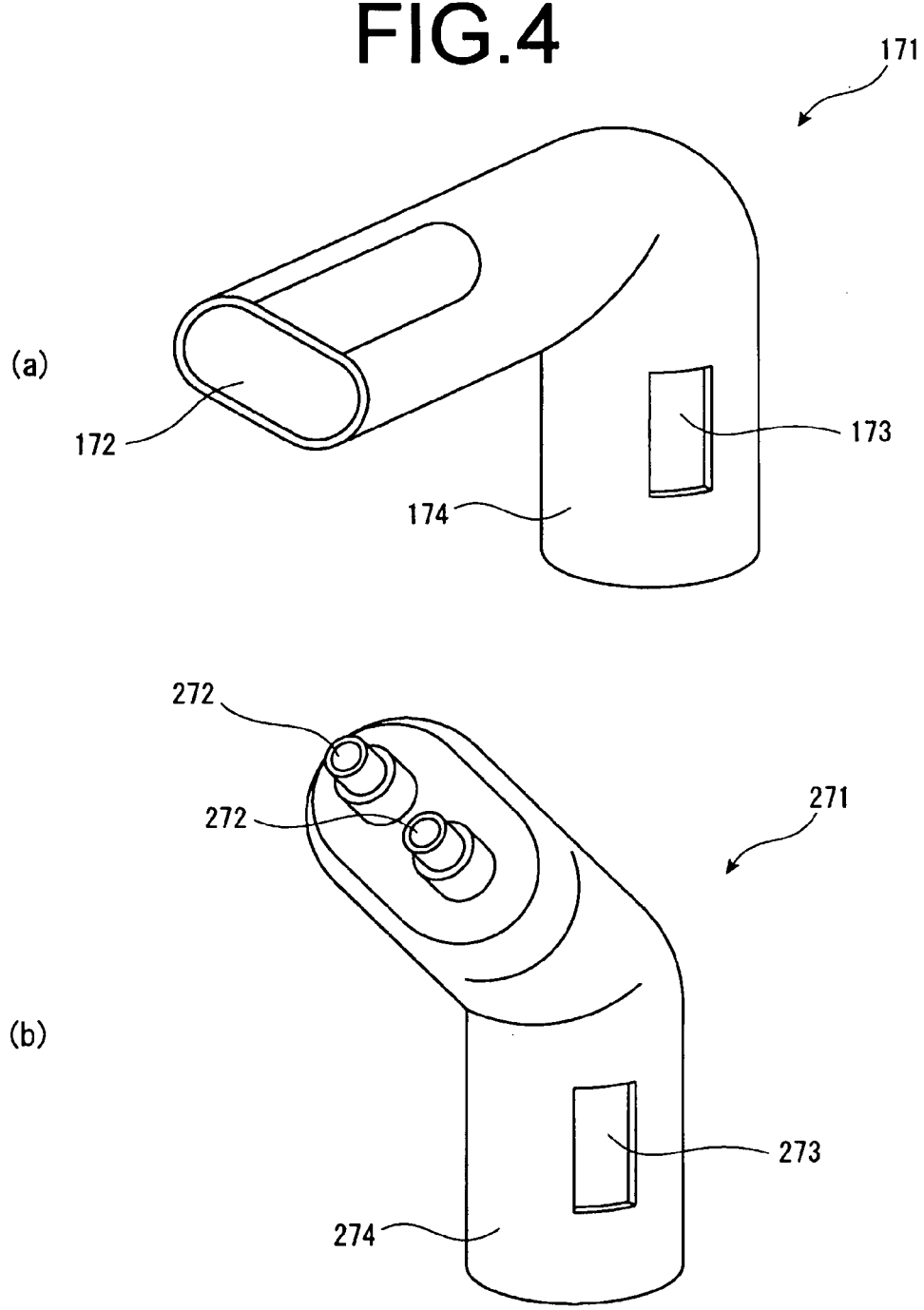
FIG. 4 A typical view showing one example of the inhalation member used to the gas mist inhaler of the invention.

FIG. 4 shows examples of other inhalations. FIG. 4(a) is a mask 171 of a mouth piece type used for breathing from the mouth only. A connecting portion 174 is connected to the gas mist supply pipe 37, and the user inhales the gas mist in the mouth from inhalation port 172. An opening port 173 may be formed. FIG. 4(b) is a nose mask 271 of a nose piece type used for breathing from the nose only. At the connecting portion 274, it is connected to the gas mist supply pipe 37, and the user inhales the gas mist into the nose from the inhalation port 272. Also, an opening port 273 may be formed.

Figure 5:
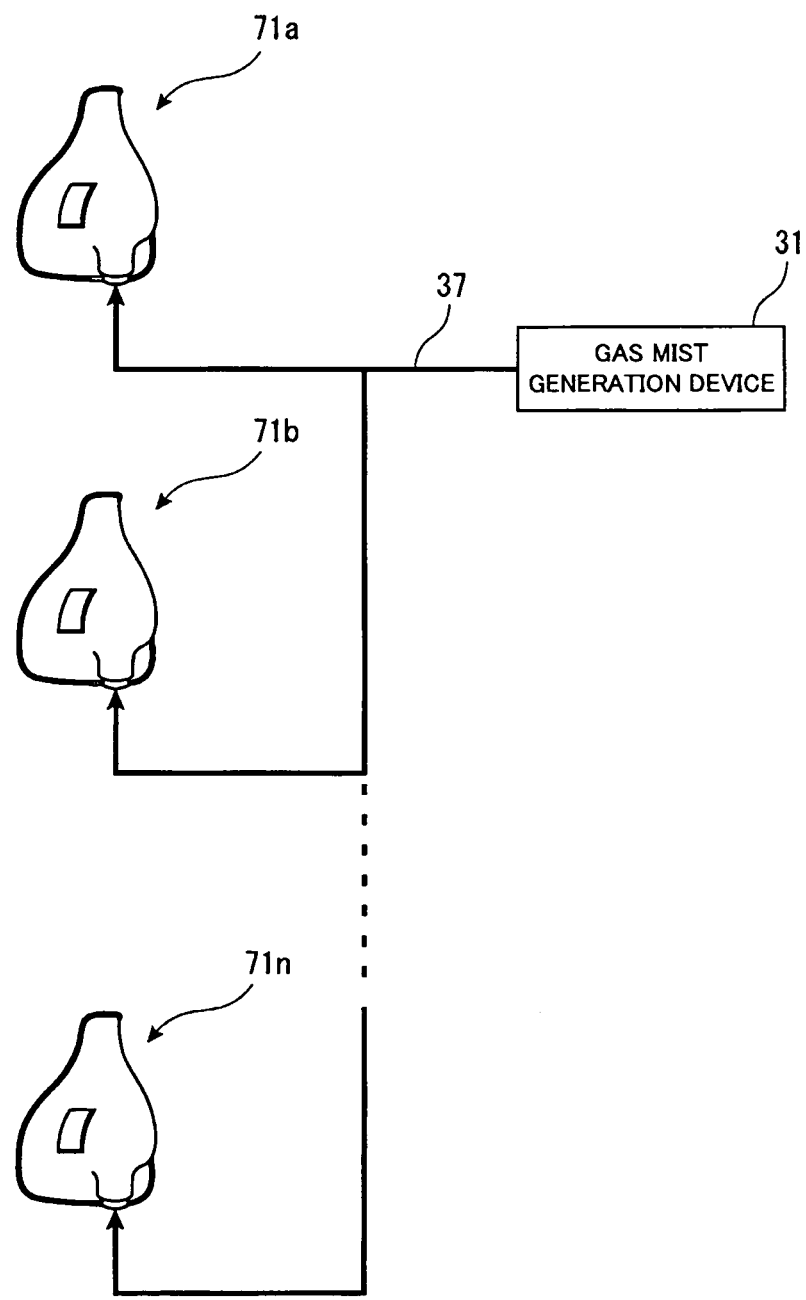
FIG. 5 A typical view showing one example using a plurality of the inhalation members in the gas mist inhaler of the invention.
Figure 6:
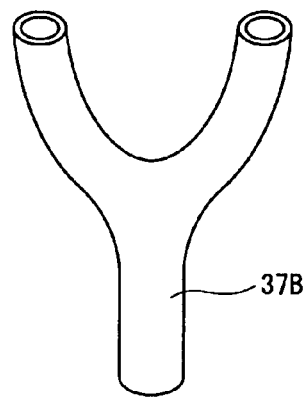
FIG. 6 A typical view showing examples of diverging forms using a plurality of the inhalation members in the gas mist inhaler of the invention.
Figure 6:
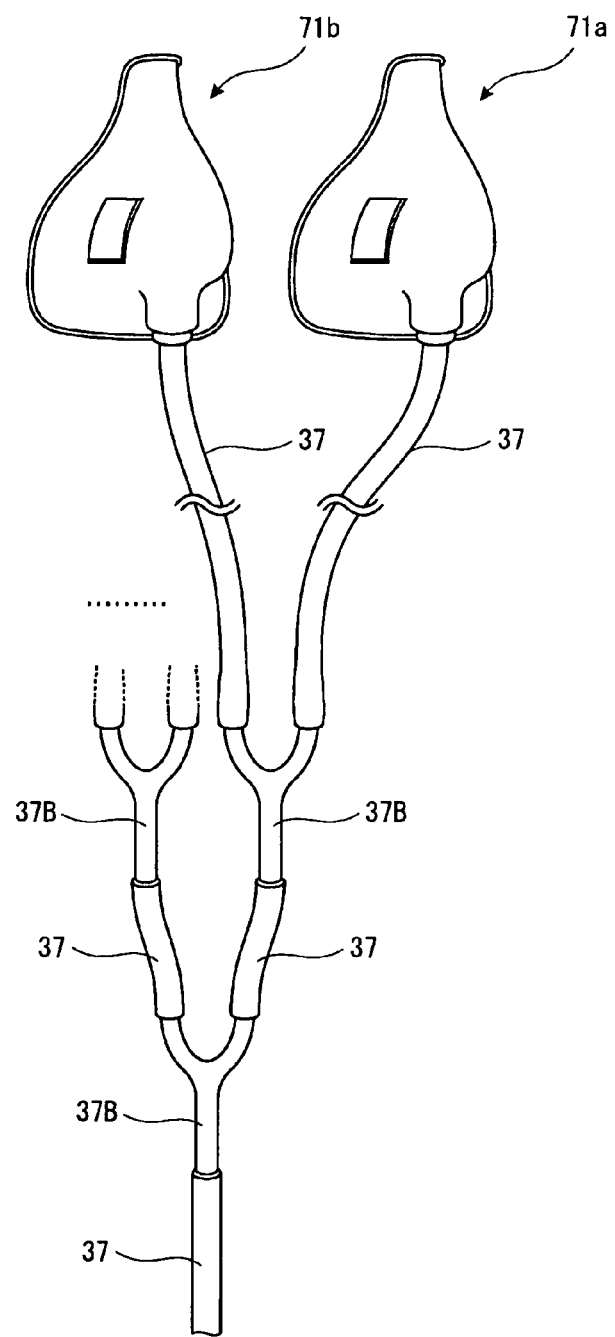

Further, the above embodiment has shown the example of connecting one inhalation mask (inhalation member) 71 to one gas mist generation device 31, and such a structure of connecting a plurality of inhalation masks 71 is available. FIGS. 5 and 6 show examples of the gas mist inhalers for using plural inhalation members. As to the same parts as those of the embodiment shown in FIG. 1, the same numerals will be given, and detailed explanation will be omitted.

As shown in FIG. 5, between the gas mist generation device 31 and the inhalation masks 71 (71a, 71b, . . . 71n), there is placed the gas mist supply pipe 37 diverging into plurality. It is thereby possible to connect the plural inhalation members 71 to the gas mist generation device 31. At this time, it is also sufficient to provide a branch pipe 37B as shown in FIG. 6(a) on the way of the gas mist supply pipe 37 to connect to the other gas mist supply pipe 37, thereby to easily branch into plurality as shown in FIG. 6(b).

Figure 7:
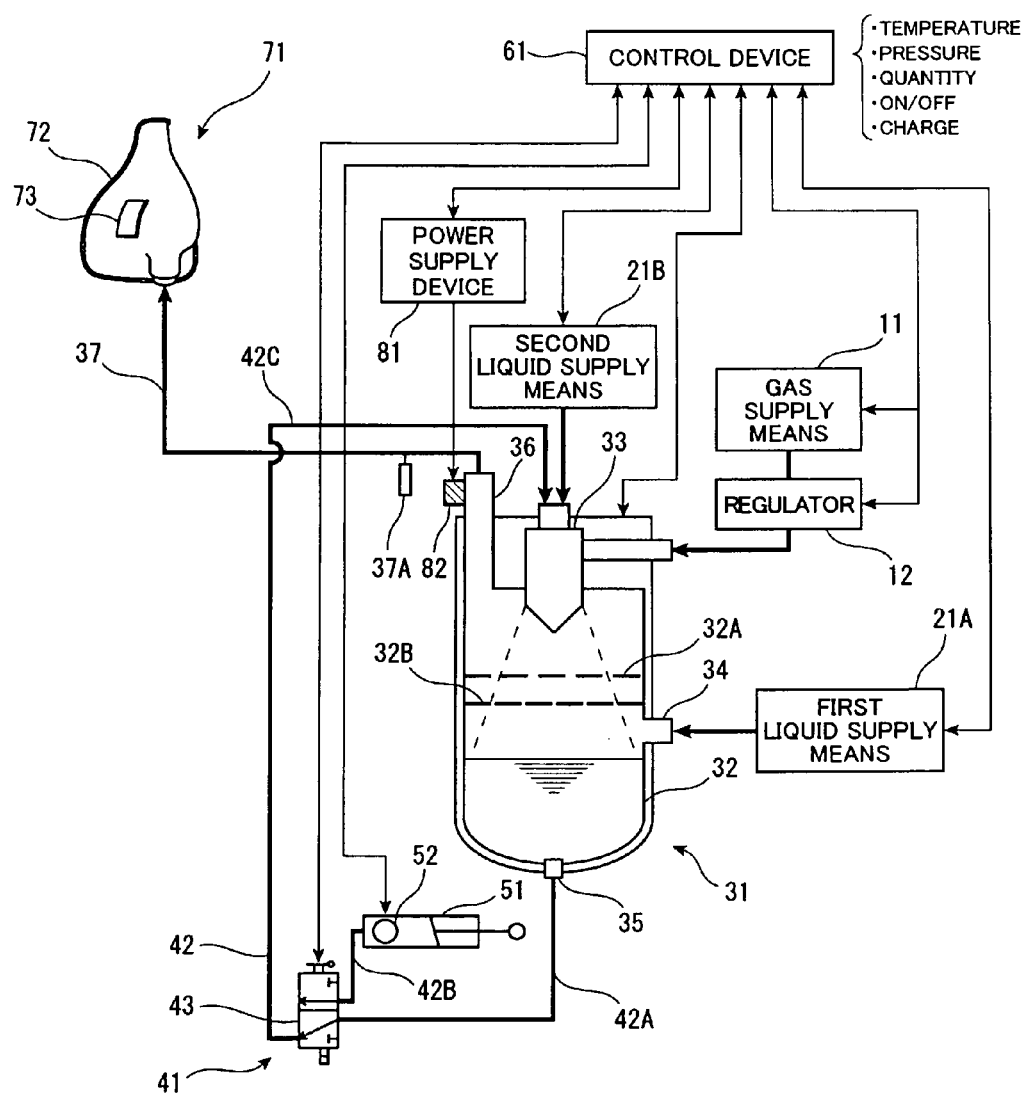
FIG. 7 A schematic view showing the whole structure of the gas mist inhaler depending on the other embodiment of the invention.

FIG. 7 is the schematic view showing the whole structure of the gas mist inhaler depending on the other embodiment of the invention. This embodiment will make explanation to a gas mist inhaler 2 having a further means for charging the generated gas mist. As to the same parts as those of the embodiment shown in FIG. 1, the same numerals will be given, and detailed explanation will be omitted.

As shown in FIG. 7, in the gas mist inhaler of this embodiment, an electrode 82 is arranged at the gas mist discharge port 36 of the gas mist generation device 31. The electrode 82 is connected to the power supply device 81 for setting voltage value and switching on-off by the control device 61.

The electrode 82 gives charge (minus charge is desirable) when the gas mist generated by the gas mist generation device 31 is discharged from the gas mist discharge port 36. Thereby, the gas mist is made electrified, and adherence to a charged substance can be heightened. For example, if heightening adherence to the mucous membrane of the living organism, it is possible to improve absorption of the gas mist and accelerate penetration of the above mentioned medicines contained in the gas mist into the mucous membrane.

As having above mentioned, according to the gas mist inhaler of the present invention, in addition to ordinary effects of the inhaler, owing to the physiological action of the gas mist, not only permeating the liquid medicine into the upper and lower airways of the living organism, also activating a blood flow around a diseased part, the invention can display effects such as rapidly moderating an inflammation or increasing immunological force.

The above reference has explained the embodiments of the invention, but is not limited to the above embodiments, and so far as not deviating from the subject matter of the invention, various kinds of embodiments are, of course, available.

INDUSTRIAL APPLICABILITY

The invention is concerned with the gas mist inhaler for carrying out the oral inhalation of the gas mist with industrial availability.

DESCRIPTION OF SYMBOLS

1, 2: gas mist inhaler
11: gas supply means
12: regulator
21A: first liquid supply means
21B: second liquid supply means
31: gas mist generation device
32: tank
32A, 32B: plates
33: fluid nozzle
34: liquid supply port
35: liquid discharge port
36: gas mist discharge port
37: gas mist supply pipe
37A: liquid drop removing filter
37B: branch pipe
37C: cornice shaped pipe
41: liquid circulation means
42: liquid circulation circuit
42A: first liquid conduit line
42B: second liquid conduit line
42C: third liquid conduit line
43: valve
51: liquid pressurizer
52: manometer
61: control device
71: inhalation mask
72: inhalation port
73: opening port
81: power supply device
82: electrode
171: mouth mask
172: inhalation port
173: opening port
174: connecting portion
271: nose mask
272: inhalation port
273: opening port
274: connecting portion

The invention claimed is:

1. A gas mist inhaler, comprising a gas supply device for supplying a gas including oxygen, carbon dioxide, or a mixed gas of oxygen and carbon dioxide, a first and a second liquid supply devices for supplying a first and a second liquids, a gas mist generation device for generating a gas mist prepared by pulverizing and dissolving the gas and the first and second liquids, the gas mist generation device including a tank for storing the first and second liquids and the gas mist, a nozzle disposed in the tank for jetting the gas mist, and a liquid discharge portion for discharging the first and second liquids stored in the tank, an inhalation member having an inhalation port for inhaling the gas mist from the gas mist generation device into a living organism, a pipe portion to be connected to the living organism and an opening for taking in outside air such that the gas mist and the outside air are inhaled into at least one of an upper air way and a lower air way of the living organism, and a liquid circulation device having a liquid circulation path, the first and second liquids stored in the tank being circulated from the liquid discharge portion to the nozzle through the liquid circulation path such that an amount of the gas dissolved in the liquid is increased through circulation thereof, wherein the tank is connected to the first liquid supply device, the nozzle is connected to the gas supply device and the second liquid supply device and disposed in a top portion of the tank, and the liquid discharge portion is disposed in a bottom portion of the tank, wherein the gas mist inhaler further comprises a liquid pressure device connected to the liquid circulation device for supplying pressurized first and second liquids to the nozzle, wherein the gas mist generation device has a gas mist discharge portion at a top portion thereof; and the gas mist with the pressurized liquids from the liquid pressure device is discharged from the gas mist discharge portion, wherein the liquid circulation path is formed of a first liquid pipe and a second liquid pipe, the first liquid pipe extending from the liquid discharge portion to the nozzle, and the second liquid pipe extending from the first liquid pipe to the liquid pressure device, wherein the liquid circulation device further includes a switching valve for switching from the first liquid pipe to the second liquid pipe or for connecting the second liquid pipe to the first liquid pipe, and wherein the tank includes an upper plate and a lower plate spaced apart from each other, each plate having pores for refining the gas mist; and a diameter of the pore of the lower plate is smaller than that of the upper plate, and the pores of the lower plate are placed out of alignment with those of the upper plate.

2. A gas mist inhaler as set forth in claim 1, further comprising a sensor for measuring conditions of supplying the gas, liquid and gas mist, and a control device for controlling the conditions based on measuring values of the sensor to supply the gas and the liquid and to generate and supply the gas mist.

3. A gas mist inhaler as set forth in claim 1, further comprising a charging device for giving charge to the gas mist supplied by the gas mist generation device.

4. A gas mist inhaler as set forth in claim 3, wherein the charge is negative.

5. A gas mist inhaler as set forth in claim 1, wherein the first and second liquids are at least one combination of water, ionic water, ozone water, physiological salt solution, purified water and sterilized and purified water.

6. A gas mist inhaler as set forth in claim 5, wherein the first and second liquids further contain at least one of menthol, vitamin E, vitamin C derivative, retinol, anesthetic, cyclodextrin, photocatalyst, complex of photocatalyst and apatite, hyaluronic acid, coenzyme Q10, seed oil, propolith, silica, povidone-iodine, anti-allergic agent, anti-inflammatory agent, anti-febrile, anti-fungus agent, anti-influenza virus, influenza vaccine, steroid agent, anti-cancer substance, and anti-hypertensive agent.

7. A gas mist inhaler as set forth in claim 1, wherein the gas mist generation device has a gas mist supply pipe for connecting the inhalation member to the gas mist generation device in order to supply the gas mist, and the gas mist supply pipe has a filter to remove liquid drops attached to an inside of the pipe.

8. A gas mist inhaler as set forth in claim 1, wherein the gas mist generation device has a gas mist supply pipe for connecting the inhalation member to the gas mist generation device in order to supply the gas mist, and at least one part of the gas mist supply pipe is composed of a cornice shaped pipe.

9. A gas mist inhaler as set forth in claim 1, wherein the gas mist generation device has a gas mist supply pipe for connecting the inhalation member to the gas mist generation device in order to supply the gas mist, and the gas mist supply pipe is provided with a check valve.

10. A gas mist inhaler as set forth in claim 1, wherein the gas mist generation device supplies the gas mist into a plurality of inhalation members.

* * * * *